United States Patent [19]

Christina et al.

[11] Patent Number: 5,010,871
[45] Date of Patent: Apr. 30, 1991

[54] PROPHYLACTIC SAFETY DEVICE

[76] Inventors: Louis J. Christina; Anna M. Christina, both of 42-30 189th St., Flushing, N.Y. 11358-2815

[21] Appl. No.: 367,354
[22] Filed: Jun. 16, 1989
[51] Int. Cl.⁵ .............................................. A61F 6/04
[52] U.S. Cl. .................................. 128/844; 128/842; 604/346; 604/347
[58] Field of Search ............... 128/842, 844; 604/346, 604/347, 349–352; 2/21

[56] References Cited

U.S. PATENT DOCUMENTS

| 2,138,626 | 11/1938 | Copen | 2/21 |
| 2,207,614 | 7/1940 | Copen | 2/21 |
| 4,354,494 | 10/1982 | Hogin | 128/844 |
| 4,576,156 | 3/1986 | Dyck et al. | 128/844 |
| 4,798,600 | 1/1989 | Meadows | 128/844 |

Primary Examiner—Robert A. Hafer
Assistant Examiner—Kerry Owens
Attorney, Agent, or Firm—Handal & Morofsky

[57] ABSTRACT

An improved prophylactic device is disclosed. The attachment of a sealing device prevents possible leakage and slippage while the proper dimensioning of the attached sealing device promotes safety along with improved performance.

6 Claims, 3 Drawing Sheets

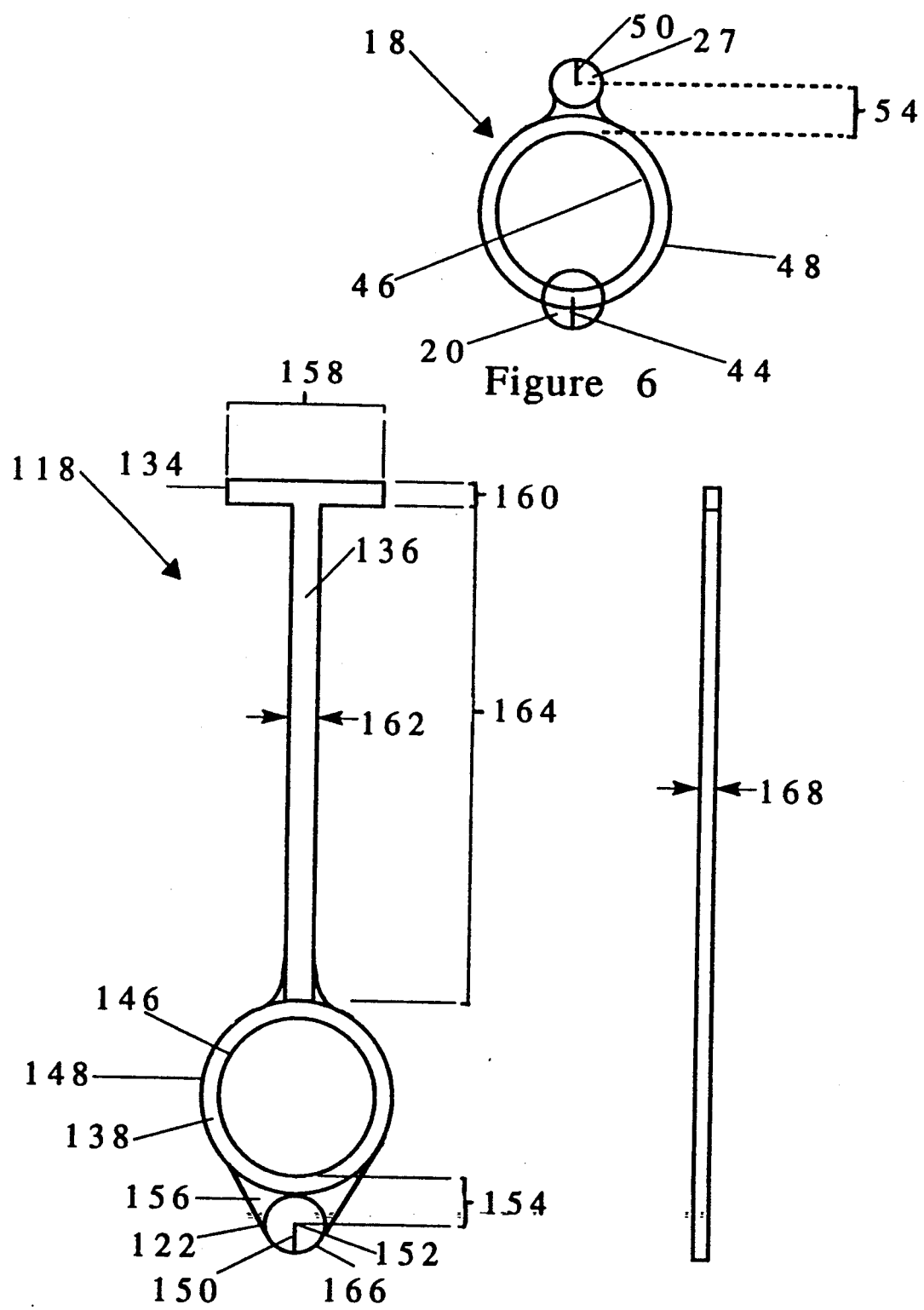

PROPHYLACTIC SAFETY DEVICE

TECHNICAL FIELD

The present invention relates to a prophylactic device designed to more effectively combat the spread of genitally transmitted disease.

BACKGROUND

The spread of the Human Immune Virus (H.I.V.) that is responsible for Acquired Immune Deficiency Syndrome (AIDS) has garnered the public attention and generated much concern and fear.

In this day and age, a disease that has a one hundred percent mortality rate is disconcerting. When such a disease is communicable, spreading and reaches the general population, there is a genuine cause for alarm.

Accordingly, AIDS has generated just such alarm. The spread of this disease among intravenous drug users and sexual partners has resulted in free-needle programs for intravenous drug users and education programs aimed at "safe sex".

The "safe sex" programs recognize and teach the effectiveness of latex condoms, when properly used, in preventing transmission of the H.I.V.

The use of such latex condoms is a reasonable measure when abstinence is not pursued. However, this measure is not perfect. In the normal course of use, there is a danger of semen seeping out the condom through migration to the condom opening. Semen also acts as a lubricant, and this may result in the condom slipping off during use.

SUMMARY OF THE INVENTION

The invention is intended to provide a remedy to the shortcomings of prophylactic devices as they now exist. By providing a better seal at the condom opening, the possibility of seepage and/or slippage is virtually eliminated.

BRIEF DESCRIPTION OF THE DRAWINGS

One way of carrying out the invention is described in detail below with reference to drawings which illustrate only two specific embodiments of the invention and in which:

FIG. 6 illustrates the dimensioning of a preferred embodiment of the safety ring of FIG. 3;

FIG. 7 illustrates the dimensioning of a preferred embodiment of the safety ring of FIG. 5, and FIG. 8 is a side view of the safety ring in FIG. 7.

BEST MODE FOR CARRYING OUT THE INVENTION

Figure 1A:
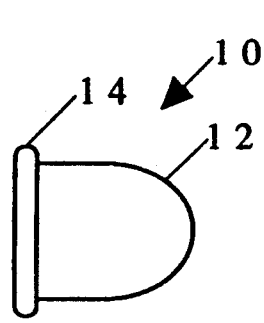
FIGS. 1a through 1e schematically depict the application of the inventive device.
Figure 1B:
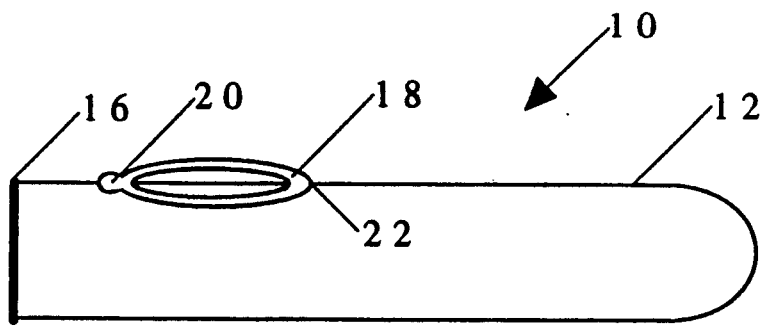
Figure 1C:
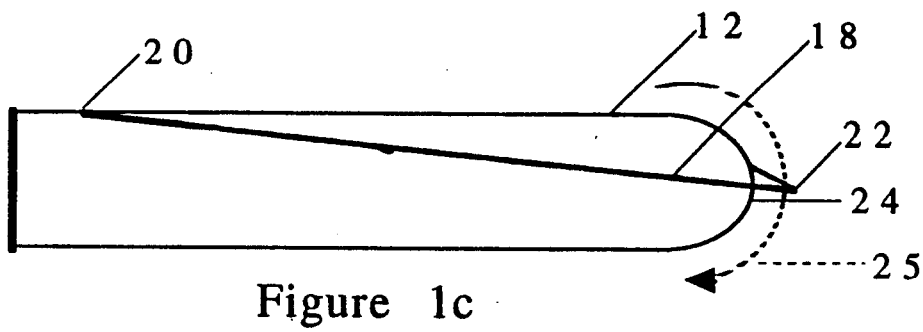
Figure 1D:
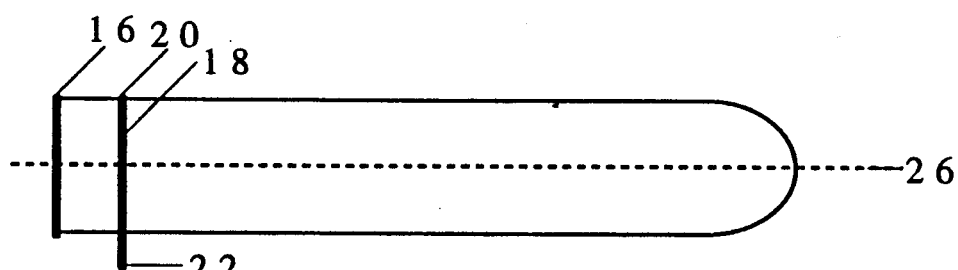
Figure 1E:
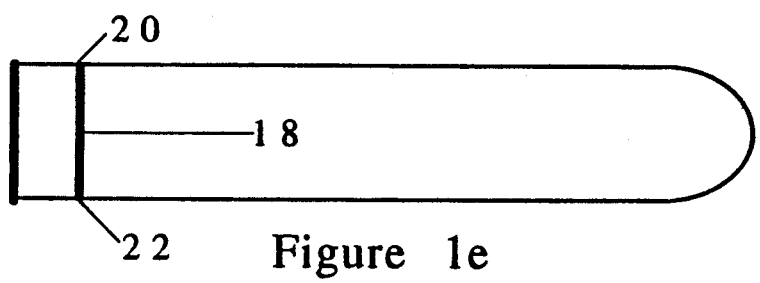

Referring to FIGS. 1a through 1e, the inventive prophylactic and the method of using it may be understood. The device 10 consists of a sheath 12 that is rolled upon itself forming roll 14. The device 10 is used with the sheath being unrolled in the conventional manner upon an erect penis (shown in phantom lines) to expose a rim 16. A safety ring 18 is now exposed, as shown in FIG. 1b. Safety ring 18 may be joined to sheath 12 at point 20. Opposite end 22 of safety ring 18 is pulled away from point 20 beyond and around sheath end 24, as illustrated in FIG. 1c by dashed arrow 25. Safety ring 18 will encircle sheath 12 once opposite end 22 has been brought around sheath end 24; after such encirclement, opposite end 22 is brought towards rim 16 until opposite end 2 is opposite point 20 with respect to the axis 26 of sheath 12, as shown in FIG. 1d. The pulling force on opposite end 22 is diminished and released, resulting in safety ring 18 contacting sheath 12 over the entire circumference of safety ring 18 and applying a constricting force around the base of the penis.

Washing or drying of the area surrounding the device is contemplated after use and before removal of the device.

Figure 2:
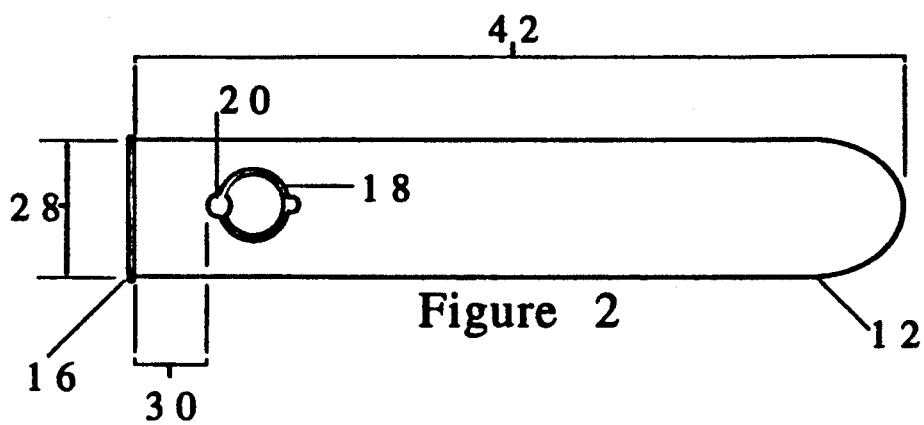
FIG. 2 is a top schematic view of the device of FIG. 1.

An unrolled device, according to the invention, and without a shaft in the sheath, may be put in a flattened state as illustrated in FIG. 2 to reveal dimensional relationships. Flattened width 28 is one half of the circumference of sheath 12 and a distance 30 may be established between rim 16 and contact point 20, as depicted in FIG. 2.

Figure 3:
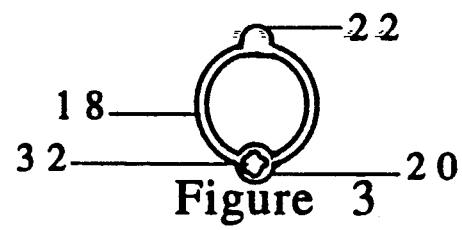
FIG. 3 is an underside view of the safety ring of FIG. 2.

Contact point 20 of safety ring 18 may be joined to sheath 12 by means of an adhesive 32. In order to obtain good adhesion to the sheath, contact point 20 may be enlarged to provide more contacting surface area for bonding to the sheath. Opposite end 22 may be enlarged to facilitate grasping as shown in FIG. 3.

Figure 4:
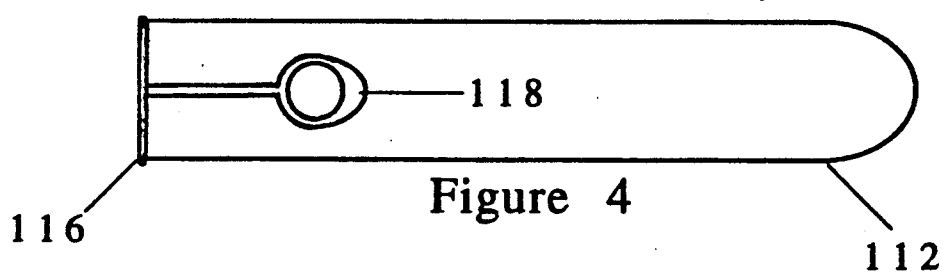
FIG. 4 is a schematic top view of the device with an alternate embodiment of the safety ring.

An alternate embodiment of the inventive prophylactic device 110 consists of a sheath 112 and a safety ring 118 whereby safety ring 118 is joined to sheath 112 at a rim 116 as shown in FIG. 4.

Figure 5:
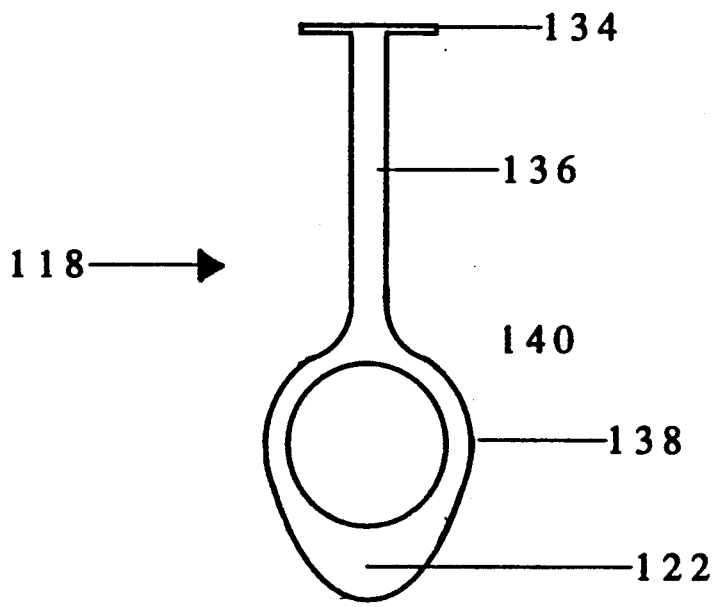
FIG. 5 is a top view of the safety ring of FIG. 4.

The alternate embodiment safety ring has a foot 134 that may be incorporated into rim 116, rim 116 being formed by rolling and fusing the open end of the sheath 112. Foot 134 is joined by stem 136 to the ring section 138 of safety ring 118 at juncture 140. Enlarging of opposite end 122 again provides for an improved grasp, as shown in FIG. 5.

The preferred embodiments use similar sheaths with a preferred flattened width 28 of approximately 50 to 55 millimeters and a length 42 of approximately 175 to 200 millimeters. Safety ring 18 is positioned on the sheath, such that a contact point 20 is at a distance from the rim 30 of approximately 35 to 40 millimeters. Contact point 20 may be circular and of radius 44. Radius 44 is approximately 4 mm in order to allow sufficient surface area for bonding between safety ring 18 and sheath 12, whether they are fused together or joined by adhesive such as Elmer's Stix-All (TM).

Safety ring 18 has an interior circumference 46 of approximately 20 millimeters in diameter and an exterior circumference 48 of approximately 25 millimeters in diameter. Opposite end 22, in this embodiment, is circular with a radius 50 of about 3 millimeters with a center 52 removed a distance 54 of approximately 4 millimeters from the interior circumference 46 and joined by stub 56.

Safety ring 118 of the alternate embodiment is joined to a sheath at foot 134. Foot 134, in this embodiment has a length 158 of approximately 15 millimeters and a width 160 of about 2 millimeters. Stem 136 has a width 162 of about 3 millimeters and a length 164 of approximately 30 to 35 millimeters.

Ring section 138 has an interior circumference 146 of approximately 20 millimeters in diameter and an exterior circumference 148 of approximately 25 millimeters in diameter. Opposite end 122 is formed of a circular section 166 with a radius 150 of approximately 4 millimeters and a center 152 removed from the inner circumference by a distance 154 of approximately 6 millimeters. Circular section 166 is joined to ring section 138 by angled stubs 156.

Both embodiments, 18 and 118, utilize an elastic rubber and have a thickness of about one-third to three-quarters of a millimeter, shown as 168 for the second embodiment, with the range of one-third to one-half millimeter thickness being preferable.

The dimensioning as described promotes snugness, assuring adequate sealing without the danger of dangerously constricting blood flow. The snugness may, however, prolong the erect state of the penis, further reducing the chances of the device slipping off the shaft.

Industrial Applicability

The inventive condom may be made by conventional means and the safety ring attached. After attachment, the device may be rolled with the safety ring lying in contact with th circumferential sidewalls of the sheath, forming a multilayer structure therewith, whereby it will be coiled into and form a part of roll 14.

While an illustrative embodiment of the invention has been described above, it is, of course, understood that various modifications will be apparent to those of ordinary skill in the art. Such modifications are within the spirit and scope of the invention, which is limited and defined only by the appended claims.

We claim:

1. A prophylactic condom comprising an open-ended sheath, said sheath comprising a rim, integral with said sheath and located at the open end of said sheath, and an attached sealing device, said attached sealing device comprising:
   (a) a foot attached to said sheath at said rim;
   (b) an elastic ring portion; and
   (c) a stem separating said foot and said elastic ring portion.

2. A prophylactic condom as claimed in claim 1, wherein said sheath is comprised of latex rubber.

3. A prophylactic condom comprising:
   (a) an open-ended latex rubber sheath;
   (b) a rolled, fused rim, integral with said sheath and located at the open end of said sheath; and
   (c) a sealing device attached at, and, at the point of attachment, made integral with said rolled, fused rim, said sealing device comprising:
      (i) a foot, said foot being incorporated into said rolled, fused rim thus achieving attachment;
      (ii) an elastic ring portion removed from said rim; and
      (iii) a stem connecting said foot and said elastic ring portion.

4. A prophylactic condom as claimed in claim 3, wherein said ring portion has an interior diameter of approximate 20 mm and an exterior diameter of approximately 25 mm and said stem is approximately 30 to 35 mm in length.

5. A prophylactic condom as claimed in claim 4, wherein said safety device has a thickness of one-third to one-half of a millimeter.

6. A prophylactic condom as claimed in claim 3, wherein said stem is of greater width at the juncture with other parts of said safety ring than in the middle of said stem.

* * * * *